US008795732B2

(12) United States Patent
Vittoria et al.

(10) Patent No.: US 8,795,732 B2
(45) Date of Patent: Aug. 5, 2014

(54) COMPOSITE MATERIAL WITH PROPERTIES OF SELF-HEALING AND RELEASE OF ACTIVE INGREDIENTS, FOR BIOMEDICAL APPLICATIONS

(75) Inventors: Vittoria Vittoria, Naples (IT); Gianfranco Peluso, Naples (IT); Loredana Tammaro, San Cipriano Picentino (IT); Liberata Guadagno, Fisciano (IT); Marialuigia Raimondo, Eboli (IT); Orsolina Petillo, Baiano (IT); Sabrina Margarucci, Pontecagnano (IT); Anna Calarco, Pozzuoli (IT)

(73) Assignee: Mario Minale, Naples (IT)

( * ) Notice: Subject to any disclaimer, the term of this patent is extended or adjusted under 35 U.S.C. 154(b) by 96 days.

(21) Appl. No.: 13/140,742

(22) PCT Filed: Dec. 14, 2009

(86) PCT No.: PCT/EP2009/008918
§ 371 (c)(1),
(2), (4) Date: Apr. 20, 2012

(87) PCT Pub. No.: WO2010/072347
PCT Pub. Date: Jul. 1, 2010

(65) Prior Publication Data
US 2012/0208895 A1 Aug. 16, 2012

(30) Foreign Application Priority Data
Dec. 22, 2008 (IT) .............................. MI2008A2284

(51) Int. Cl.
*A61K 9/16* (2006.01)
*A61K 6/00* (2006.01)
*A61K 6/08* (2006.01)
*A61C 13/00* (2006.01)

(52) U.S. Cl.
USPC ........... 424/489; 433/167; 433/180; 523/115; 523/116; 525/107

(58) Field of Classification Search
None
See application file for complete search history.

(56) References Cited

U.S. PATENT DOCUMENTS

| 5,476,142 A | * | 12/1995 | Kajita | ............................ | 166/294 |
| 2002/0007959 A1 | * | 1/2002 | Kaltenborn et al. | ...... | 174/137 B |
| 2008/0193557 A1 | * | 8/2008 | Reynolds | ....................... | 424/602 |
| 2008/0287566 A1 | * | 11/2008 | Musikant et al. | ............. | 523/118 |
| 2008/0300340 A1 | * | 12/2008 | Gross et al. | .................... | 523/120 |

FOREIGN PATENT DOCUMENTS

| WO | WO 2007/010584 A2 | 1/2007 |
| WO | WO 2008/147366 A1 | 12/2008 |
| WO | WO 2009055772 A1 * | 4/2009 |

OTHER PUBLICATIONS

MM Caruso, BJ Blaiszik, SR White, NR Sottos, JS Moore. "Full Recovery of Fracture Toughness Using a Nontoxic Solvent-Based Self-Healing System." Advanced Functional Materials, vol. 18, 2008, pp. 1898-1904.*
MM Caruso, BJ Blaiszik, SR White, NR Sottos, JS Moore. Title Page for "Full Recovery of Fracture Toughness Using a Nontoxic Solvent-Based Self-Healing System." Wiley Online Library, http://onlinelibrary.wiley.com/doi/10.1002/adfm.200800300/abstract, 2 printed pages, accessed Jun. 25, 2013, available Jul. 9, 2008.*
U Singh, S Deveraj, I Jialal. "Vitamin E, Oxidative Stress, and Inflammation." Annvual Reviews in Nutrition, vol. 25, 2005, pp. 151-174.*
S.R. White et al., "Autonomic Healing of Polymer Composites", Nature vol. 409, Feb. 15, 2001, Macmillan Magazines Ltd., pp. 794-797 and correction vol. 415, Feb. 14, 2002, p. 817.
E.N. Brown et al., "In situ poly(urea-formaldehyde) microencapsulation of dicyclopentadiene", Journal of Microencapsulation ISSN 0265-2048, Taylor & Francis Ltd. Nov.-Dec. 2003, vol. 20, No. 6, pp. 719-730.
E.N. Brown et al., "Fracture Testing of a Self-Healing Polymer Composite", Experimental Mechanics, vol. 42, No. 4, Dec. 2002, pp. 372-379.
B.J. Blaiszik et al., "Self-Healing Polymers and Composites", Annual Review of Materials Research 2010, vol. 40, pp. 179-211.

* cited by examiner

*Primary Examiner* — Frederick Krass
*Assistant Examiner* — Isaac Shomer
(74) *Attorney, Agent, or Firm* — Arent Fox LLP

(57) ABSTRACT

This invention relates to a composite material for biomedical applications, in particular dental applications, which possesses self-healing capacity and is able to incorporate a system for the release of active ingredients at the stage of application and use.

11 Claims, 6 Drawing Sheets

MTT test

MC3T3-E1

MTT test

MDPC-23

MC3T3-E1

MDPC-23

MC3T3-E1

MDPC-23

COMPOSITE MATERIAL WITH PROPERTIES OF SELF-HEALING AND RELEASE OF ACTIVE INGREDIENTS, FOR BIOMEDICAL APPLICATIONS

CROSS-REFERENCE TO RELATED APPLICATION

This application is a National Stage entry of International Application No. PCT/EP2009/008918, Dec. 14, 2009, which claims priority to Italian Patent Application No. MI2008A 002284 filed Dec. 22, 2008, the disclosure of the prior Applications are incorporated in its entirety by reference.

This invention relates to a composite material for biomedical applications, in particular dental applications, which possesses self-healing capacity and is able to incorporate a system for the release of active ingredients at the stage of application and use.

STATE OF THE ART

The scientific and technological progress of the last few years has led to the design and manufacture of innovative biomedical materials for use in the reconstruction of irremediably damaged tissues. Particular emphasis has been given to research into prosthetic materials able to restore the damaged tissue both anatomically and functionally, without causing adverse reactions at the implant site. The possible causes of failure are associated with pathological problems of infection, and an inadequate response by the material to the stresses to which it is cyclically subjected.

Modern material science, in the dental and maxillofacial field, for example, aims to achieve two main objectives:
- to design innovative devices able to preserve the viability of the dental pulp structures, at the same time preventing the onset of pulpar alterations caused by chemical-physical stimuli or bacterial noxae;
- to prevent the formation of fractures in the material used and/or between the dentine and the filling with new materials capable of "self-healing".

The ideal restoration material should maintain its structural integrity, even in the long term, and withstand mechanical stresses, wear and tear, and corrosive attack by the oral fluids. Inorganic materials have mainly been used to date, including:
- Calcium hydroxide [$Ca(OH)_2$]
- Simple zinc oxide-eugenol cements (ZOE), consisting of a zinc oxide, magnesium oxide and zinc acetate or stearate powder (under 1% as accelerator) and a liquid consisting of 85% eugenol with olive oil and glacial acetic acid (as accelerator). Modified ZOE cements are those with added plasticisers or EBA (ethoxybenzoic acid). In both cases, these modifications seem to enhance the biocompatibility properties, and increase the physical properties of resistance and insulation.
- Zinc phosphate cements, consisting of zinc oxide powders (90%), magnesium, calcium and silicon powders (10%), and a liquid component consisting of an aqueous solution of 50% orthophosphoric acid with the addition of zinc or aluminium phosphate.
- Polycarboxylate cements, consisting of a mixture of zinc oxide powder with not more than 10% magnesium or tin oxide and a liquid phase formed by a 30-45% aqueous solution of polyacrylic acid (pH 1-1.6) or an itaconic or maleic acid copolymer thereof.
- Glass-ionomer cements
- Compound paints (liners), which are suspensions of calcium hydroxide and zinc oxide combined with resin powder or cellulose in a volatile liquid vehicle.
- Cavity paints or varnishes, which are liquid solutions consisting of a natural resin (copal, resin) or synthetic resin dissolved in a particularly volatile organic solvent (alcohol, acetone, chloroform or ether).

The suitability of a restoration material is mainly determined by its ability to achieve stable adherence to the dental substrate and permanent interpenetration, with no gaps and/or porosity, between its edges and the extracellular matrix with which it comes into contact. A lasting hermetic seal would prevent pathogenic micro-organisms, toxins, oral fluids and food residues from penetrating below the restoration, compromising its efficacy and causing further pulp damage [Downer et al., 1999]. Finally, to prevent inflammation of the pulp from being caused by the intrinsic toxicity of the material or its constituents, a new compound must necessarily undergo biological validation before marketing and clinical use.

The materials cited above have many limitations and adverse effects.

Composite resins were recently introduced. This name refers to materials formed by combining a synthetic polymer with inorganic ceramic particles. The polymer forms the matrix of the composite in which the inorganic particles that act as strengthener (filler) are dispersed. The two substances combine chemically due to the action of a suitable binding agent (or bonding agent) applied to the surfaces of the filler particles. The simultaneous presence of the matrix and filler generates a material with better characteristics than the individual constituents.

The organic phase of most of the composites now on the market consists of the chemical compound synthesised by Bowen, known as "Bowen's resin". Bowen's resin consists of a succession of monomers, each of which derives from a synthesis reaction between bisphenol A and two molecules of glycidyl methacrylate. The monomer BIS-GMA forms three-dimensionally crosslinked polymers by reaction of addition of the methacrylic groups; the result is a resin with very different behaviour from unmodified acrylic resins.

The BIS-GMA monomer is highly viscous, and therefore generally diluted with different monomers or oligomers with a low molecular weight (known as "viscosity controllers") so as to achieve adequate fluidity and better incorporation.

Said diluents are:
- triethylene glycol dimethacrylate (TEGDMA), the most commonly used;
- ethylene glycol dimethacrylate (EGDMA);
- diurethane dimethacrylate (DUEDMA);
- bisphenol A methacrylate (BIS-GMA);
- methyl methacrylate (MMA).

Unfilled fluid resins, commonly called bonding resins, which are essential to promote adherence between the tissue and the composite, usually contain a preponderant quantity of monomer. Inorganic pigments designed to give the materials the most suitable shades of colour are also dispersed in the matrix; they include titanium dioxide and iron oxides. In some products, the monomer UEDMA (urethane dimethacrylate) completely replaces BIS-GMA, while in others it is associated with BIS-GMA and/or TEGDMA: the absence of OH groups reduces hydrophilia; NH groups should promote adherence through the formation of hydrogen bonds. The binding agent keeps the resinous material adhering to the inorganic material (matrix-filler bond). The most common method is the use of an organic silicon-based adhesive called silane, with which the inorganic particles are coated, to make a "bridge" between matrix and filler. Small amounts of binder are sufficient under ideal conditions, such as aqueous solutions containing 0.025-2% of silane, to coat the particles of filler so as to make a continuous polysiloxane network that protects the filler from water penetration and ensures equal distribution of the mechanical stresses between matrix and inorganic filler. However, it has been observed that silane often does not form an even film, and this offers an entry point for small water molecules which attack the filler surface not completely coated by silane molecules, causing a reduction in the overall resistance of the composite. The most widely used bonding agent is methacryloxypropyltrimethoxysilane.

The inorganic phase of the composites is formed by tiny mineral particles incorporated in the resinous matrix. The filler of composite dental resins is currently represented by barium glass, quartz glass and pyrogenic silica in the vast majority of the cases. Vitreous materials are preferred in view of their transparency, which facilitates the diffusion of light, and due to the possibility of creating new formulations, which can make the composite radio-opaque or contain fluoride, for example, so that the material performs a protective action for the dental and bone tissue.

CLOSEST PRIOR ART

Patent application WO 2008/147366 discloses synthetic dental restorative composites having self-healing characteristics. The composites comprise a polymeric matrix wherein microspheres encapsulating a monomer are dispersed. A catalyst is present in the composite to polymerize the encapsulated monomer when a fracture ruptures the microspheres. The composites may also contain at least two microspheres: one microsphere that encapsulates a polymer with a curing site along with a crosslinking agent; and a second microsphere that encapsulates a polymerisation catalyst. The crosslinking agents may be organotin catalysts, platinum compounds and hydride-functional siloxanes.

The composites of WO 2008/147366 present several drawbacks. In all of the examples reported in this document the elements responsible for the self-healing effect are microcapsules filled with dicyclopentadiene (DCPD) and Grubbs catalyst powders dispersed in the matrix. These constituents present drawbacks which make the product unsuitable for medical, and especially dental applications:

a) the dark colour given to the resin by the catalyst powders (Grubbs catalyst). These ruthenium complexes give the resin a very dark colour (purple-brown);

b) the particular monomer chosen as self-healing agent is a cyclic olefin which presents considerable difficulties due to the fact that even extremely small amounts (which could come into contact with the organic mucous membranes) are harmful, and also have a very unpleasant, penetrating, persistent odour (the same drawback is presented by norbornene and all derivatives thereof);

Tin- or platinum based crosslinking agents are known to be toxic compounds and they are not safe for dental applications. In particular, microspheres filled with stannous octooate (example 24 of WO 2008/147366) are extremely harmful to the health, especially due to the serious irritation it can cause to the respiratory tract, eyes and skin, and its teratogenic effects.

Moreover, the self-healing function of the materials described in WO 2008/147366 is not associated with an active constituent release function.

SUMMARY OF THE INVENTION

This invention relates to a biomedical material which presents functions additional to those described; said functions give the material a self-healing capacity and the possibility of incorporating slow-release active ingredients, in optimal or sub-optimal concentrations with regard to eliciting a pharmacological activity, at the stage of application and use.

One aspect of this invention is therefore a self-healing composite material for biomedical applications comprising a polymer matrix containing a self-repair system consisting of microspheres or nanospheres of a polymer material filled with an oligomeric curing agent which polymerises in the presence of a suitable activator (catalyst or initiator), dispersed in the matrix. When, during use, a fracture is propagated in the polymer matrix positioned in situ, the microspheres open, allowing the exit of the curing agent which polymerises, filling the cavity formed by the fracture and thus repairing the material.

Another aspect of the invention is the incorporation in said self-healing composite material of a system of fixing and release of active ingredients, able to modulate—e.g. elicit—a pharmacological response on target cells, depending on the concentration of the active ingredient, said system comprising an inorganic constituent dispersed in the polymer matrix of the self-healing composite material, and is characterised by the ability to Incorporate active ingredients for applications in the medical and dental field, establishing strong and/or weak bonds with them. An interpenetration mixture and/or compound is thus obtained, with ions or active ingredients in ionic or molecular form being inserted in the inorganic structure. These ingredients, the choice of which depends on the medical and/or dental application in question, can be released slowly at the site where the matrix is positioned and where such release takes place at sub-optimal or locally-effective concentrations, they are able to restore the morpho-functional integrity of the extracellular matrix (e.g. repository of calcium or fluoride ions in the stromal acellular component of the bone or dental tissue).

Pharmacologically active compounds such as anti-inflammatory, antibiotic or chemotherapeutic agents may also be incorporated in the micro- or nanospheres and they may be released following fractures or by applying physical energy such as shock waves or ultrasounds.

A further aspect of the invention is the use of said composite material to make prosthetic materials or materials for the reconstruction of tissue, especially damaged dental tissues, in view of the ability of said material of improving the performance of the fillers, cements or resins currently used for such a purpose in the dentistry or orthopaedic field.

A further aspect of the invention relates to products containing said composite material which take the form of dental resins, cements or prostheses.

Finally, a further aspect of the invention relates to the use of the composite materials for the preservation of biological specimens of archaeological interest, for example bones, so as to avoid degradation of the same.

DESCRIPTION OF THE INVENTION

Figure 1:
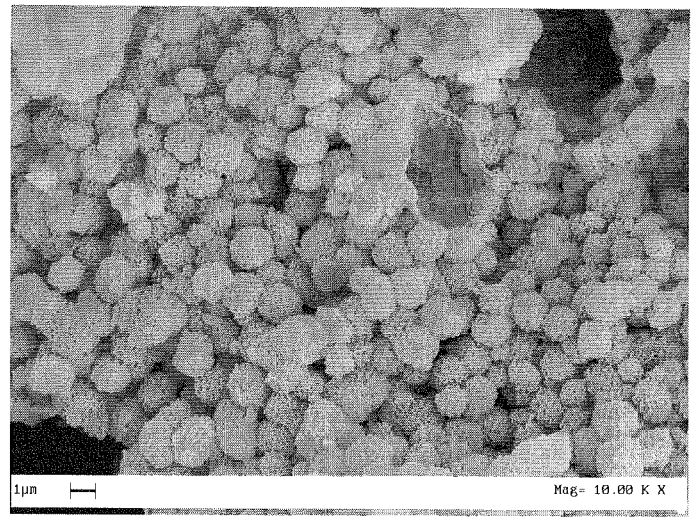
FIG. 1 is an image of synthesized microcapsules filled with a curing agent according to aspects of the invention.

This invention relates to the field of composite polymer materials with a thermoplastic and thermosetting matrix.

Polymers with structural functions in the medical and dental field (such as dental resins or prostheses) are used in applications wherein they may be subjected to great mechanical strains which cause damage due to the formation of hairline cracks, even in the innermost parts of the structure. Composite materials which are self-healing, ie. independently develop a repair process which restores the integrity of the matrix before the hairline cracks can propagate, seriously compromising the integrity of the structure, have already been proposed in other fields (such as structural materials in the aeronautical industry).

Composite materials of this type are described in U.S. Pat. No. 6,518,330. In particular, ring-opening metathesis reaction catalyst powders, and microcapsules containing a reactive monomer able to polymerise following a ring-opening metathesis reaction and subsequently crosslink, are dispersed in the matrix of these materials. Thus when a crack that forms in said material reaches a microcapsule, it breaks it, causing the release of the monomer. When the monomer comes into contact with the catalyst, it polymerises and then crosslinks so as to fill the crack and restore the structural continuity of the matrix. The patent literature reporting these self-healing composite materials shows that the purpose has been achieved by a thermosetting resin specifically designed for application in the aeronautical industry, as reported in Italian patent applications no. TO2008A000194 filed on Mar. 13, 2008 and no. TO2008A000723 filed on Oct. 22, 2008, both by Alenia Aeronautica. In this case, the self-healing process involves the presence in the resin of Grubbs and Hoveyda catalysts, which are toxic substances often endowed with genotoxic and protumorigenic action.

The insertion of the components on which the self-healing function is based in a resin suitable for use as a dental sealant and/or cements for dental crowns or veneers in general presents serious difficulties due to the aesthetic properties of the material (these materials give the resins a dark colour), its toxicity, and/or the hardening conditions of the material, which require treatments at high temperatures (not typical of the oral cavity) and/or complex operations not feasible under the usual conditions in which dental sealants are applied. These problems have prevented the widespread use of these materials in dentistry.

The purpose of the invention is to provide a self-healing composite material for uses in the medical and dental field, which performs better, especially as regards the toxicity and self-healing capacity of the material under the conditions in which said self-healing activity is to be performed (temperature, humidity, ionic strength, pH, mechanical stresses, etc.) and can incorporate a system for the release of the active ingredients.

According to a first aspect of the invention, this purpose is achieved by dispersing in a polymer matrix, preferably chosen from those generally used in the dental field, the constituents essential to give the resin self-healing properties. Said constituents are (A) micro- or nanocapsules containing a curing agent and (B) a single constituent or a constituent in a mixture external to the microcapsules, distributed evenly in the polymer matrix, and able to activate the curing and/or crosslinking reaction in hairline cracks which arise following damage under the conditions present in the oral cavity and under the mechanical stress of mastication. Pharmacologically active ingredients may optionally be present in the microcapsules.

In the composite material according to the invention, the micro- or nanocapsules contain a curing agent whose chemical nature is strongly dependent on the composition of the polymer matrix, and especially on the agent used to activate curing.

The curing agent consists of oligomers which crosslink when they come into contact with an activator (catalyst or initiator) of the curing and/or crosslinking reaction.

The oligomer can be a precursor of a thermosetting resin which can belong to various classes of materials, such as epoxy resins like phenol-glycidyl ethers, glycidylamines, cycloaliphatic resins and multifunctional resins, in particular diglycidyl ether of bisphenol A (DGEBA), polyglycidyl ether of phenol-formaldehyde novolac, polyglycidylether of o-cresol-formaldehyde novolac, N,N,N',N'-tetraglycidyl methylenedianiline, bisphenol A novolac, triglycidylether of trisphenol-methane, triglycidyl p-aminophenol, 3,4-epoxycyclohexylmethyl-3,4-epoxycyclohexane carboxylate.

An oligomer precursor of epoxy resins, preferably a liquid precursor of an epoxy resin based on bisphenol A (BPA), is preferably used as curing agent.

Said precursors contain an oxirane structure which, through contact with a suitable catalyst or initiator, allows the conversion of the oligomer to a solid which is insoluble and infusible during the self-healing processes.

In particular, bisphenol A diglycidyl ether of formula I was used in a preferred embodiment of the composite according to the invention:

Formula I

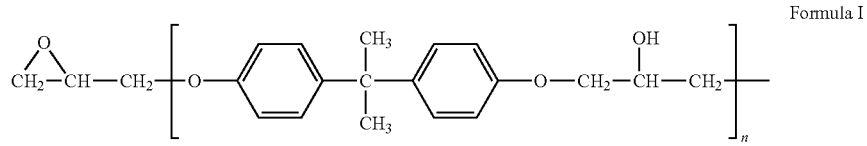

wherein n<2.5.

This compound constitutes a non-limiting example of epoxy resin precursors which can be used according to the invention; with epoxy precursors having a higher value of n, it is preferable to modulate the viscosity by mixing the oligomer with a reactive diluent to allow the curing agent to flow and fill the cracks. Non-limiting examples of reactive solvents which can be used are 1,4 butanediol diglycidyl ether, neopentyl glycol diglycidyl ether, nonylphenol glycidyl ether, 2-ethylhexyl glycidyl ether, and cyclohexane dimethanol diglycidyl ether.

The micro- or nanocapsules containing the curing agent can be synthesised with a variety of materials and different micro- or nanoencapsulation methods well known to one skilled in the art. Non-limiting examples of materials with which the micro- or nanocapsules filled with curing agent can be synthesised are copolymers of maleic anhydride and poly-urea-formaldehyde, polyurethanes, isocyanates with diamines and triamines, and polyamides, as reported in U.S. Pat. No. 6,518,330.

The microencapsulation or nanoencapsulation techniques which can be used are interfacial curing, complex coacervation and curing in situ. BPA was encapsulated in the composite according to the invention by the in situ curing process with urea-formaldehyde. Said process allows the walls of the microcapsules to be synthesised with a thickness such as to modulate the rigidity thereof in relation to that of the matrix.

An image of synthesised microcapsules filled with curing agent, having a diameter of a few microns and obtained by curing in situ with urea-formaldehyde, is shown in FIG. 1 of example 1. The nanometric dimensions of the microcapsules can be obtained by controlling the process parameters in a suitable way well-known to one skilled in the art.

The activators dispersed evenly in the polymer matrix may be catalysts or initiators. The catalysts or initiators are chosen on the basis of the chemical nature of the curing agent; preferred catalytic species are: 2,4,6-tris(dimethylaminomethyl) phenol, triethylenediamine, N,N-dimethyl-piperidine, benzyldimethylamine, 2-(dimethylaminomethyl)phenol and 2-dimethylaminoethanol (DMAE). Hardeners selected from imidazoles, dicyandiamines, or a mixture of polyamide and tertiary amines mixed with polyols as disclosed in U.S. Pat. No. 6,987,161 B2 can also be used.

Different types of hardener can be used for curing agents consisting of oligomer precursors of epoxy resins. "Hardener" means a substance or mixture of substances added to the starting oligomer or monomer to allow crosslinking. Said substances may take part in the crosslinking reaction (and will be "structural members" of the cross-linked polymer) or may simply promote the crosslinking reaction (in which case they are not part of the cross-linked polymer). A hardener which is not involved in the crosslinking reaction (but merely promotes it) is also called a catalytic hardener.

The curing agents used for the resin hardening process can be a) primary and secondary polyamines and adducts thereof; b) polyamides; and c) anhydrides.

Preferred crosslinking agents are: aromatic diamines, aliphatic amines such as diethylenetriamine, triethylenetetramine, tetraethylenepentamine, diethylaminopropylamine and N-aminoethylpiperazine; commercial products such as Epicure 3125, Epicure 3140, Epicure 3155, Epicure 3192 (or mixtures thereof) or Versamid 100 and Ancamide 100, Versamid 115 and Ancamide 220, Versamid 125 and Ancamide 260 A; phthalic anhydride, bicyclo[2,1]-5-heptane-2,3 dicarboxylic anhydride, and methyltetrahydrophthalic anhydride.

For the purpose of the invention the hardener chosen must be able to cure the epoxy resins (and consequently harden them via the crosslinking reactions) at low temperature, and give them good thermal properties and excellent mechanical strength. This latter aspect is very important, because one of the properties which the crosslinked polymer designed to repair microfractures in the event of damage must have is mechanical and thermal resistance comparable with those of the matrix. Examples of hardeners and activators able to cure epoxy resin precursors at low temperatures, even at 20° C. (producing crosslinked products with a Tg value of between 60 and 65° C.), are given in U.S. Pat. No. 6,987,161 B2. Said hardeners and activators are, for example, imidazoles, dicyandiamines, or a mixture of polyamide and tertiary amines mixed with polyols, and mixtures thereof.

Figure 2:
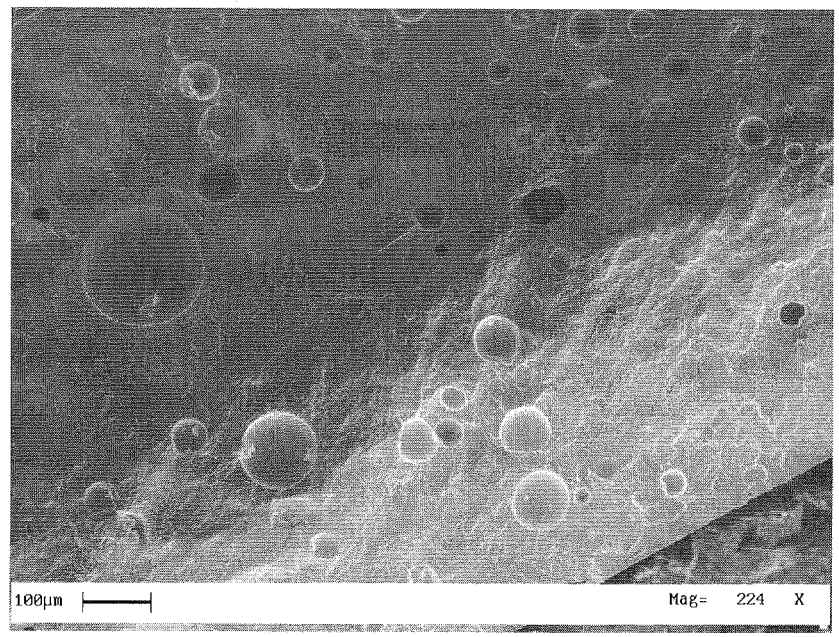
FIG. 2 is an image of a cross-section of a self-healing specimen with microcapsules an 2-dimethylaminoethanol (DMAE) distributed in a polymer matrix according to aspects of the invention.

Specimens of self-healing resin were prepared using different primary, secondary and tertiary amines including diethylenetriamine, tetraethylene pentamine, 2,4,6-tris(dimethylaminomethyl)phenol, triethylenediamine, N,N-dimethylpiperidine, benzyldimethylamine, 2-(dimethylamino-methyl)phenol and 2-dimethylaminoethanol (DMAE). DMAE was used as catalyst for homopolymerisation in a preferred embodiment of the invention. The image of a cross-section of the self-healing specimen with microcapsules and DMAE distributed in the polymer matrix is shown in FIG. 2 of example 2.

The polymer used for the matrix can be chosen without any particular limitations, e.g. among phenol, amide, epoxy, polyurethane, unsaturated polyester, cyanoacrylic, silicone, alkyl, acrylic, polycarbonate, polyester, thermoplastic, vinyl ester, vinyl polyfluoride and polyolefin resins.

In particular, the following can be used in the dental field: 2,2-Bis[4-(2-hydroxy-3-methacryloxypropoxy)phenyl]propane (Bis-GMA); Bis-GMA ethoxylate (EBPDMA); 1,6-bis-[4-(2-hydroxy-3-methacryloxypropyl)phenyl]propane, ethyl 4-(N,N-dimethylamine)benzoate (EDMAB); triethylene glycol dimethacrylate (TEGDMA); 3,4-epoxy-cyclo-hexylm-ethyl-3,4-epoxycyclohexane carboxylate (EPC); 1,6-bis-[2-methacryloyloxyethoxycarbonylamino]-2,4,4-trimethylhexane (UDMA); dodecanediol dimethacrylate (D3BUT); Spiro orthocarbonates (SOC); cyclic ethers; cyclic acetals and allyl sulphides; vinylcyclopropanes; branched and dendritic resins; resins; compomers: ormocers; fluorinated Bis-GMA analogues.

In a further aspect of the invention, the composite self-healing material incorporates a system of anchorage of active ingredients, which can be released slowly over time. The anchorage and release system of this particular aspect of the invention is characterised in that the active ingredients are fixed to an inorganic compound by strong bonds (ie. covalent or ionic bonds) and/or weak bonds (ie. van der Waals interactions). The resulting inorganic solid/active ingredient system is then incorporated in the self-healing composite material to which the invention relates.

Release systems consisting of a polymer matrix with no self-healing properties and an inorganic component able to fix active constituents through ion bonds are described in PCT/IT2006/000556.

For the purpose of this invention, an active ingredient is any substance which has useful effects in the medical field in general and the dental field in particular. Examples of active ingredients, to be released in pharmacologically optimal or sub-optimal amounts include calcium, fluoride, zinc, strontium phosphate or phosphonate ions, or an organic ion with the properties required for a specific use.

For the purpose of this invention, inorganic compounds to which the active ingredients are anchored may be lamellar inorganic solids with intercalation properties (see chapter 1 of Volume VII of Comprehensive Supramolecular Chemistry, Pergamon Press, Oxford, 1996), especially those with a negative charge of the lamellae, counterbalanced by cations inserted in the interlamellar region (known as cationic lamellar solids) and those with a positive charge, counterbalanced by anions inserted in the interlayer region (called anionic lamellar solids) ("interlamellar" and "interlayer" can be considered synonymous). Non-limiting examples of the former are cationic clays (montmorillonite, vermiculite, fluorohectorite, bentonite) and zirconium or titanium phosphates, which are able to intercalate, by means of a cation exchange process, active ingredients which contain in the molecule a site that can be converted to a cation, generally an amine site able to give a quaternary ammonium cation. The latter include synthetic hydrotalcites, also known as anionic clays or double lamellar hydroxides (because two cations are present in the layer, e.g. $Mg_6Al_2(OH)_{16}CO_3$, which can intercalate, via an anion exchange process, active ingredients with sites which can provide anions, typically carboxyl, phenol, sulphonic and phosphonic groups. The preferred matrices for intercalation of anionic drugs are Mg—Al or Zn—Al synthetic hydrotalcites with a molar ratio Mg(Zn)/Al ranging from 1.5 to 4, and an anion exchange capacity ranging from 2 to 5 mequiv/g.

In the case of hydrotalcite, the lamellar solid derives from brucite $Mg(OH)_2$ by Mg/Al substitution, which creates an excess positive charge, offset by the anions present in the tunnels (e.g. $Cl^-$ or $NO_3^-$). The charge depends on the extension of the Mg/Al substitution, and is expressed as charge density, which determines the anion exchange capacity (mequiv/g). The general formula of synthetic hydrotalcites or double lamellar hydroxides can be written as formula (II):

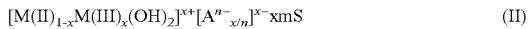

$$[M(II)_{1-x}M(III)_x(OH)_2]^{x+}[A^{n-}{}_{x/n}]^{x-}\cdot mS \qquad (II)$$

where M(II) is a metal of valency (II), preferably selected from Mg, Zn, Co, Ni, Mn and Cu; M(III) is a metal of valency (III), preferably selected from Al, Cr, Fe, V and Co; $A^{n-}$ is an anion with a negative charge n, which offsets the charge and is preferably selected from $Cl^-, NO_3^-, CO_3^{--}, SO_4^{--}$, organic anions; m is the number of molecules of solvent, generally water, co-intercalated (S), by formula weight of the compound. The number of moles x of cation M(III) by formula weight of the compound generally ranges between 0.2 and 0.40, and its value determines the charge density of the layer and the anion exchange capacity. The number of moles of co-intercalated solvent, m, is normally between 0 and 2, depending on the nature of A and the degree of intercalation (e.g. $0.6H_2O$). Systems wherein a plurality of bivalent cations (e.g. Mg and Cu) or a plurality of trivalent cations (e.g. Al and Cr) is present in the interval of x considered are always classed as hydrotalcite-like compounds. Equally, for the purpose of this invention, the double hydroxide of formula $Al_2Li(OH)_2A^{n-}{}_{1/n}$ is classed as a lamellar inorganic compound.

Inorganic compounds with no charge are zeolites, boehmites and alkoxy silanes, which can give rise to cyclical and cubic Si—O—Si structures (POSS). Finally, allotropic forms of carbon, such as fullerenes, and carbon nanotubes (single, double or multiple wall, functionalised and non-functionalised) are considered.

It has surprisingly been observed that the incorporation of the inorganic compound according to this aspect of the invention in the polymer resin with self-healing characteristics improves its mechanical properties (e.g. modulus of elasticity and breaking energy), thermal properties (e.g. increase in glass transition temperature and thermal breakdown temperature) and permeability to liquids, gases and vapours, consequently allowing the manufacture of products with a high mechanical modulus and good tenacity. In the case of resins, there is a surprising increase in the glass transition temperature, Tg, indicating better crosslinking when the inorganic compound is present.

The active ingredients can be: fluoride ions, calcium ions, diphosphonates, phosphates and others chosen as required. The release of the active constituents can be modulated in a wide range, as regards both the quantity of active ingredients fixed on the inorganic compound and those released at variable times. Moreover, the fixing method, with strong and/or weak bonds, allows the release of the active ingredient only through deintercalation processes, the kinetics of which depend on the chemico-physical parameters of the contact solution (e.g. ionic strength of the solution, pH, temperature, etc.). This is consequently a system of anchorage of active ingredients which can be released if required, but only in the presence of particular interactive environments. The release can therefore be modulated in a wide range of situations, and is adaptable to specific requirements.

The method for the preparation of the release system is a multistage process which involves the preparation of a pre-mixture comprising the lamellar inorganic solid and the active ingredient. The pre-mixture, preferably in the form of micro- and nanoparticles, is then mixed with the precursors of the polymer matrix according to known techniques. In some cases the active ingredient is already present in the lamellar compound which exists in nature (e.g. calcic bentonite, which contains calcium ions).

The intercalation compound can be characterised by thermogravimetry measurements, which supply the quantity of inorganic residue after thermal breakdown at 800° C. (the quantity of active ingredient present in the mixture is obtained by subtraction), and X-ray diffractometry analysis, which demonstrates the intercalation of the active molecule.

The choice of inorganic solid depends on the polymer matrix with self-healing characteristics, and above all on the type of active molecule. When the organic molecule has been chosen, the parameters which can be varied relate to the type of lamellar inorganic solid. Solids with a negative charge of the lamellae (smectic clays, and Zr(Ti) lamellar phosphates) will be used for cationic active ingredients, and solids with a positive lamellar charge (natural or synthetic hydrotalcite) will be used for anionic active ingredients. Both types of solid are present in the form of a microcrystalline powder with dimensions which can vary, typically in an interval of approx. 0.01-100 μm or 1-50 μm, and preferably 0.1-10 μm or 30-50 μm.

The parameters to be taken into consideration when preparing the anchorage and controlled-release system according to this aspect of the invention are:
1) Type of precursor of self-healing polymer system;
2) Concentration of intercalation compound in the self-healing polymer matrix. Said concentration can advantageously range between 0.1% and 40% by weight of inorganic substance containing the active molecule;
3) Type of incorporation process, the conditions of which are chosen by one skilled in the art according to his knowledge.

When the release system according to the invention has been obtained, and incorporated in the precursor of the self-healing resin, the precursor can be subjected to crosslinking processes (e.g. photo-crosslinking) to obtain the products for the final use.

The parameters, on which the kinetics of release of the active ingredients depend, in amounts determined on the basis of the biological need, can be modulated and controlled in a wide range, and with the indications given in the text and his own know-how, one skilled in the art will be able to find the best conditions for implementing the invention. Generally, the aspects to be evaluated are:
1) Type of active ingredient;
2) Type of inorganic material to which the active ingredient is anchored, by means of strong bonds (covalent, ionic) or weak bonds;
3) Concentration of the active species anchored to the inorganic compound;
4) Type of self-healing resin or polymer matrix;
5) Concentration of complex (active-inorganic species) in the self-healing polymer matrix.

It is therefore evident that by appropriately choosing and controlling the parameters described, products suitable for numerous applications in the field of reconstructive dental surgery can be made.

Moreover, depending on the percentages of lamellar solid present in it, the system according to the invention acquires unexpected mechanical properties (increased compression, temperature and traction resistance, increased modellability, even of complex forms). The enhanced physical characteristics of the invention also allow products in concentric layers to be obtained which, due to their surface and thickness and concentration of lamellar solids, are able to anchor and allow release for different times.

Typically, the fixing and release system of this aspect of the invention comprises approx. 50-99% by weight of resin (i), preferably approx. 50-80% or 60-90%, more preferably approx. 80-90% or 80-99%; the inorganic component (ii) containing the active constituent interpenetrated and/or absorbed on the surface is present in a quantity of between approx. 1-40% by weight, preferably approx. 10-20% or 10-40%, and more preferably approx. 10-20% or 20-1%.

The quantity of ion or active ingredient compared with the inorganic constituent is preferably given by the following expression:

Load(g/g)=α×MW/(FW+α×MW) where alpha is the degree of interpenetration, defined as the number of moles of active ingredient interpenetrated and/or absorbed by 1 mol of inorganic constituent, MW is the molecular weight (g/mol) of the active ingredient, and FW is the formula weight (g/mol) of the inorganic constituent not including the active ingredient. The active ingredient (iii) is preferably present in the quantity of between approx. 1-50% by weight, more preferably approx. 20-50%, even more preferably approx. 40-50% compared with the inorganic constituent. This percentage is naturally associated with the molecular weight of the ion or active ingredient.

In a particular embodiment of this aspect of the invention, the system of fixing the ions or active ingredients is organised in at least two or more mixed parts, wherein the individual parts comprise interpenetration compounds and different active ingredients. Said system allows a number of active ingredients to be fixed simultaneously, to perform different functions.

Another aspect of the invention is the use of the self-healing composite material according to the invention, optionally containing the ion and active ingredient fixing system, to make resins for applications in the medical, and especially the dental field.

Another aspect of the invention is products made of or coated with a single or multi-ply coating of the self-healing composite material according to the invention, optionally containing the anchorage and release system.

Another aspect of the present invention is the encapsulation in the micro- and/or nanocapsules of pharmacologically active molecules, such as, for example, growth factors, anti-inflammatory agents, antibiotics, fungicides, antimicrobial agents, anti-fibrinolytic agents, chemotherapeutic agents and biotherapeutics. The release of such products can occur at the same time of the fracture process or can be induced by physical agents such as ultrasounds or shock waves.

Further aspects will become clear from the following detailed description of the invention.

EXAMPLE 1

Microcapsules consisting of polyurea-formaldehyde containing the precursor of the epoxy resin were prepared by curing in situ in a water-oil emulsion. 400 mL of deionised water and 100 mL of an aqueous solution of an EMA copolymer were mixed in a 2 L beaker at ambient temperature (25° C.). 10 g of urea, 1.0 g of ammonium chloride and 1.0 g of resorcinol were dissolved in the solution under stirring. The pH was increased from 2.6 to 3.5 by adding NaOH and HCl drop by drop. A slow flow of 120 ml of epoxy oligomer was added to form an emulsion, and stabilised for 10 min. After stabilisation, 25 g of an aqueous solution of formaldehyde was added. The emulsion was heated at the rate of 1° C. a minute to 55° C. After 4 hours' continuous stirring the heating was switched off and the mixture cooled. The suspension of microcapsules was separated under vacuum, and the microcapsules were rinsed and dried for 48 hours. The SEM image of the microcapsules obtained is shown in FIG. 1.

EXAMPLE 2

6 g of bis GMA (containing 10% of DMAE as homopolymerization activator and/or a primary aromatic diamine for crosslinking the epoxy) was mixed with 600 mg of the microcapsules previously prepared. Circular and rectangular specimens were photopolymerised by exposing them to light in the visible spectrum. These specimens were fractured and subjected to scanning electron microscopy analysis, after metallisation. FIG. 2 shows the SEM image of a cross-section of one of these specimens. The image clearly shows the presence of the microcapsules, still partly intact.

EXAMPLE 3

Solid urea was added to 0.5 mol/dm³ of a solution of metal chlorides, having a molar fraction M(III)/[M(III)+M(II)] amounting to 0.33, until the urea/[M(II)+M(III)] molar ratio reached the value 3.3. The clear solution was heated, under stirring, at temperatures between 60 and 100° C. All materials collected showed X-ray diffractograms typical of compounds belonging to the hydrotalcite (HTlc) family, the general formula of which can be written as

where M(II) can be Mg, Zn, Co, Ni, Mn, etc.; M(III) can be Al, Cr, Fe, V, Co, etc.; $A^{n-}$ is the anion which compensates the charge and can be $Cl^-$, $NO_3^-$, $CO_3^{--}$, $SO_4^{--}$, organic anions, etc.; m is the number of molecules of co-intercalated solvent (S), by formula weight of the compound. The number of moles x of cation M(III) by formula weight of the compound generally ranges between 0.2 and 0.33, and its value determines the charge density of the layer.

In the case of the present example, we obtained a compound of formula:

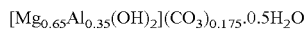

determined by elemental analysis (Sample A). The suspension was titrated with 0.1M HCl in a solution of 0.1M NaCl in a pHstat, and kept under stirring for 24 hours. It was then centrifuged, and the moist solid was washed three times with distilled water and decarbonated, then stove dried. The crystalline solid was X-ray analysed to check that the exchange between the carbonate ion and the chloride ion had taken place. Elemental analysis demonstrated that the compound obtained (Sample B) was:

[$Mg_{0.65}Al_{0.35}(OH)_2$]$Cl_{0.35}$×$0.6H_2O$

To obtain the nitrate form, sample B was suspended in an 0.5 M solution of $NaNO_3$ for 24 hours. The solid recovered was washed three times with deionised, decarbonated water, and dried on a saturated solution of NaCl (relative humidity, R.H., 75%). The compound obtained has the formula [$Mg_{0.65}Al_{0.35}(OH)_2$]($NO_3$)$_{0.35}$×$0.68H_2O$ (Sample C).

EXAMPLE 4

The sample C obtained in example 3 was suspended for two days under nitrogen flow, under stirring at ambient temperature, in a solution of 0.25M NaF in decarbonated water. The solid recovered was filtered, washed three times with decarbonated water, and dried on a saturated solution of NaCl (relative humidity, R.H., 75%). The compound obtained has the formula [$Mg_{0.65}Al_{0.35}(OH)_2$](F)$_{0.35}$×$0.7H_2O$ (Sample D).

EXAMPLE 5

Sample D obtained in example 4 was mixed at concentrations of 0.7%, 5%, 10% and 20% w/w with resin Bis-GMA (RK) loaded with microcapsules (see Example 2); the composite obtained was then cured by photopolymerisation. The samples are called RKFx, where x is the percentage by weight of sample D in resin RK.

EXAMPLE 6

Figure 3:
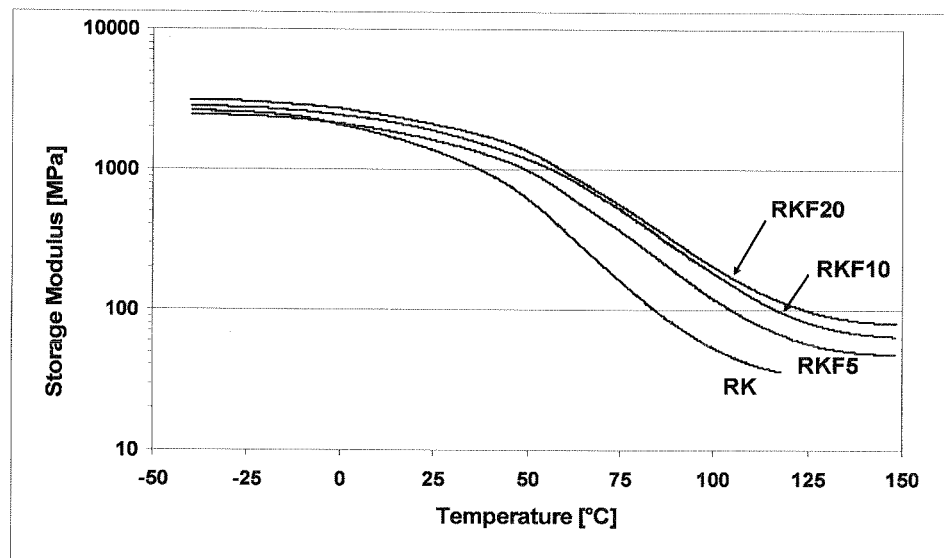
FIG. 3 is a graph showing storage modules as a function of temperature for resins contraining fluorinated inorganic solids and microcapsules (RKFx) according to aspects of the invention.
Figure 4:
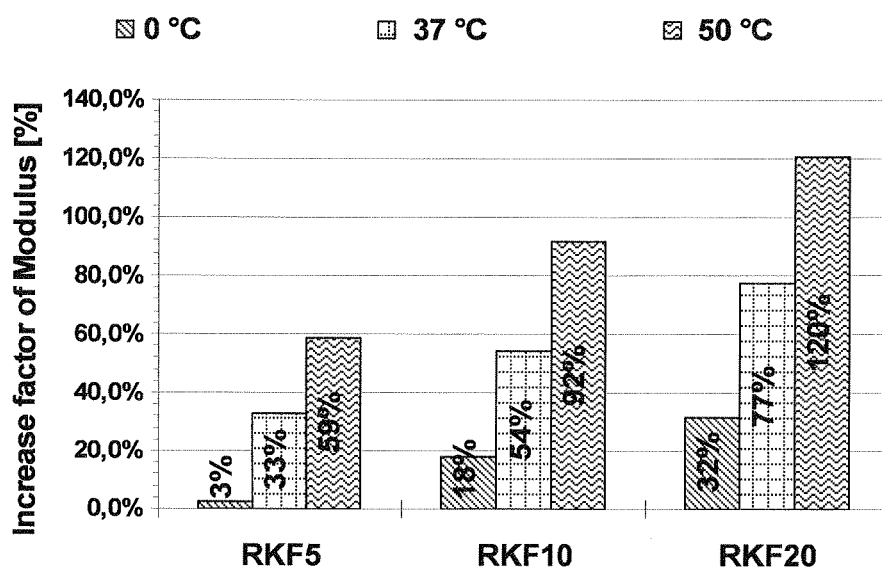
FIG. 4 is a bar chart showing increase of the modules at various temperatures for compositions RKF5, RKF10 and RKF20 according to aspects of the invention.

The study of the mechanical properties in a wide temperature range demonstrated that the values of the modulus of elasticity of the resins containing the fluorinated inorganic solid and the microcapsules (RKFx) increased compared with the resin as is (RK) (FIG. 3). This increase, which was evident after the glass transition temperature, was observed at different temperatures and for different compositions (FIG. 4).

EXAMPLE 7

The resin was suspended in saline solution and the release of the active ingredient was monitored over time.

Figure 5:
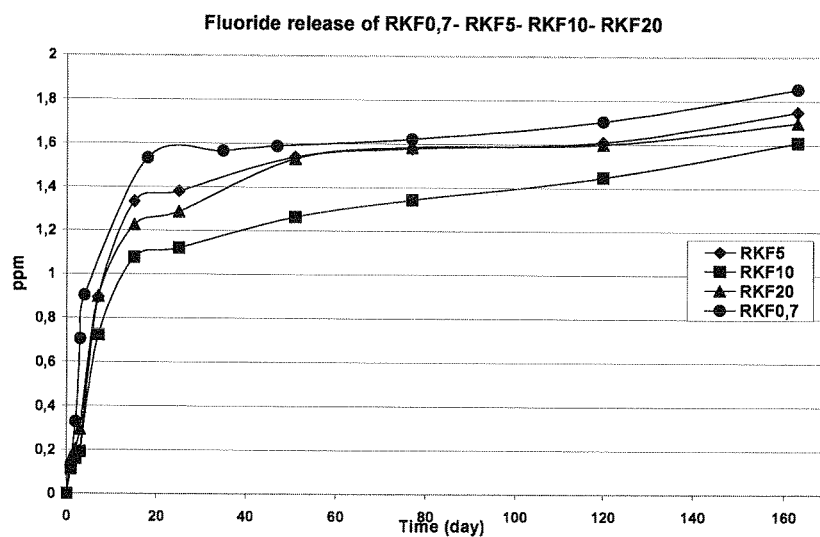
FIG. 5 is a graph showing the release of fluoride ion at various initial concentrations in the resin according to aspects of the invention.

A significant phenomenon was observed which constitutes a further advantage of the system according to the invention: the anchorage of the active molecule to the inorganic lamellar compound allows slower release. This makes the system according to the invention much more efficient. FIG. 5, as an example, shows the release of fluoride ion at various initial concentrations in the resin.

Figure 6:
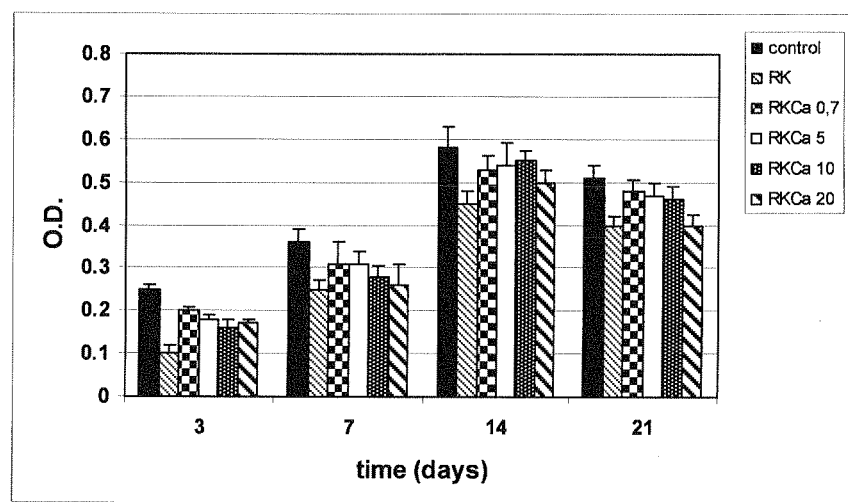
FIG. 6 is a bar chart showing the cytotoxic effect (MTT test) of compositions according to aspects of the invention on osteoblast cells of line MC3T3-E1.
Figure 7:
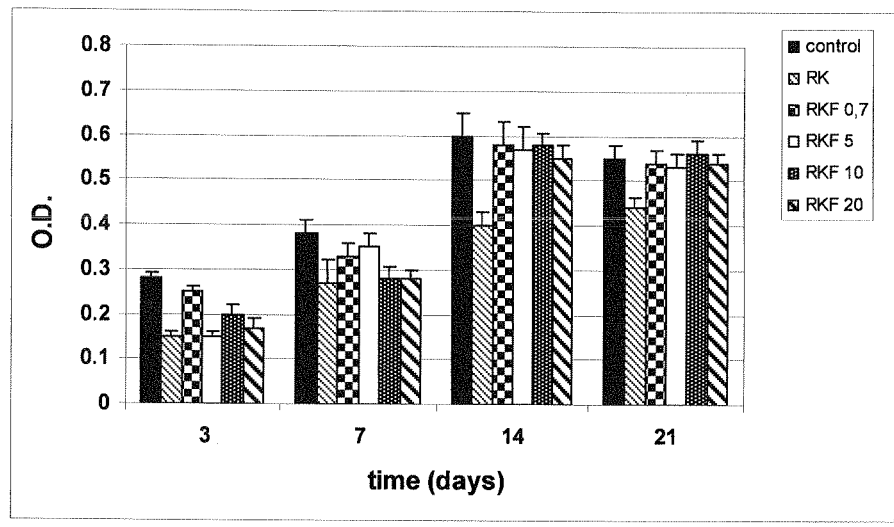
FIG. 7 is a bar chart showing the cytotoxic effect (MTT test) of compositions according to aspects of the invention on osteoblast cells of line MDPC-23.

We set out below the results of a study designed to evaluate the in vitro response of the materials to which this invention relates on osteoblast cells of line (MC3T3-E1) in the case of materials loaded with calcium (RKCa), and odontoblast cells of line (MDPC-23) in the case of materials loaded with fluoride (RKF). The cells were cultured in α-modified medium, with the addition of 10% bovine serum, 100 units/ml of antibiotics (penicillin/streptomycin), ascorbic acid (50 µg/ml) and sodium β-glycerophosphate (2 mM). The cells, cultured in the absence (control) and presence of the materials to which this invention relates, were examined after 7 days (confluence) and 14 days (mineralisation). The cytotoxic effect (MTT test) and degree of differentiation (activity of alkaline phosphatase ALP and collagen I) were evaluated in the presence of the materials to which this invention relates. The data relating to the study conducted are shown in FIGS. 6 and 7.

The results demonstrate the absence of cytotoxic effects for the materials tested, compared with the control.

Alkaline Phosphatase (ALP) Activity and Collagen Content

Figure 8:
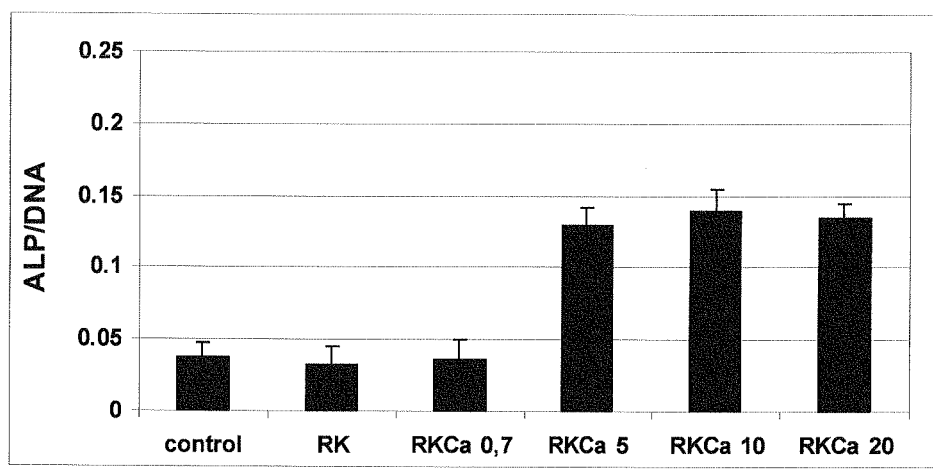
FIG. 8 is a bar chart showing for MC3T3-E1, alkaline phosphatase (ALP) activity normalized in relation to total DNA for compositions according to aspects of the invention.
Figure 9:
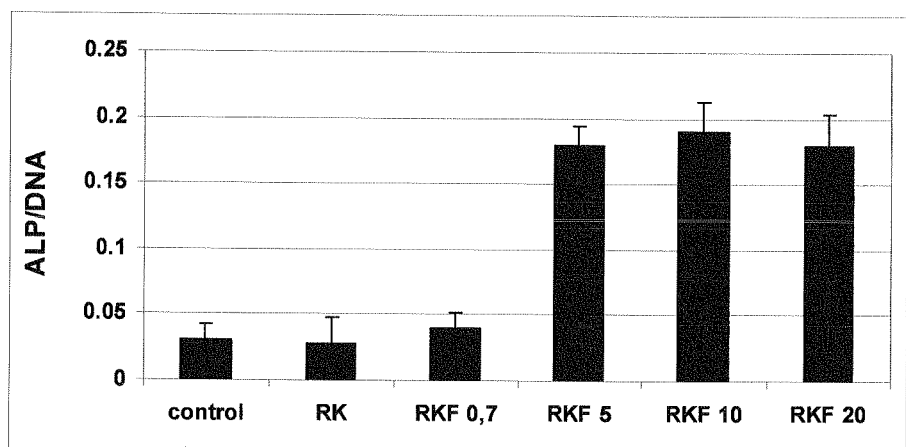
FIG. 9 is a bar chart showing for MDPC-B 23, alkaline phosphatase (ALP) activity normalized in relation to total DNA for compositions according to aspects of the invention.
Figure 10:
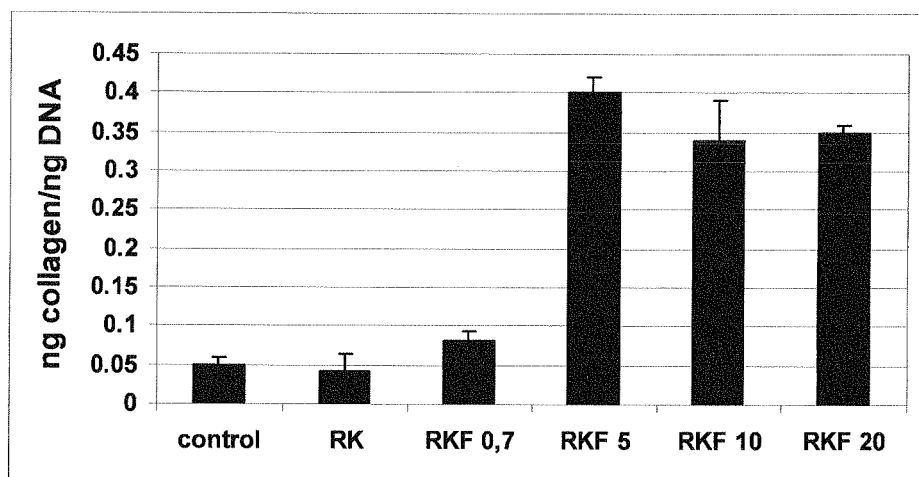
FIG. 10 is a bar chart showing MC3T3-E1, the total collagen content for compositions according to aspects of the invention.
Figure 11:
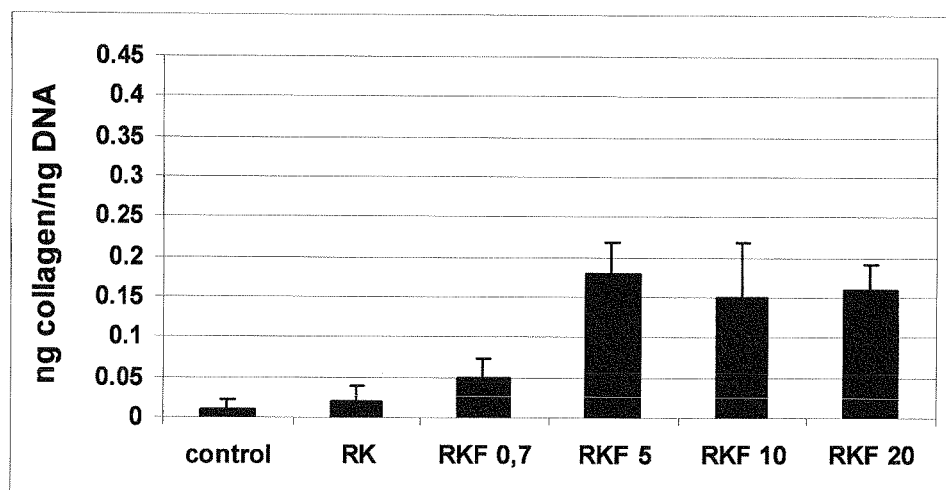
FIG. 11 is a bar chart showing for MDPC-23, the total collagen content for compositions according to aspects of the invention.

The total proteins were extracted and collected by centrifugation, and the precipitate obtained was resuspended in 0.5 ml of acetic acid. The collagen synthesised was measured using the "Sircol Collagen Assay", and the quantity was read on the spectrophotometer at 540 nm. The alkaline phosphatase activity was evaluated by "ALP20 reagent" in accordance with the manufacturer's instructions. Both values were normalised in relation to the total DNA. The results are shown in FIGS. 8 and 9, while the total collagen content is shown in FIGS. 10 and 11.

The results indicate that both the calcium on cells MC3T3-E1 and the fluorine on cells MDPC-23 have a stimulating effect on the alkaline phosphatase activities and on type I collagen production, typical cell differentiation markers for both lines used.

The invention claimed is:

1. A method of using a dental prosthesis or cement, comprising the step of contacting a dental prosthesis or cement with tissue in the mouth of a patient, wherein said dental prosthesis or cement comprises a self-healing composite material comprising:
    a) a polymeric matrix;
    b) microspheres or nanospheres containing a polymerising agent; and
    c) a curing agent selected from the group consisting of diethylenetriamine, tetraethylenepentaneamine, tris(dimethyl-aminomethyl)-phenol, triethylenediamine, N,N-dimethylpiperidine, benzyldimethylamine, 2-(dimethylaminomethyl)phenol and 2-dimethylaminoethanol;
    wherein the polymerising agent of part (b) is selected from the group consisting of phenol-glycidyl ethers, glycidylamines, diglycidyl ether of bisphenol A, polyglycidyl ether of phenol-formaldehyde novolac, polyglycidylether of o-cresol-formaldehyde novolac, N, N, N', N'-tetraglycidyl methylenedianiline, bisphenol A novolac, triglycidylether of trisphenol-methane, triglycidyl p-aminophenol,3,4-epoxycyclohexylmethyl-3,4-epoxycyclohexane carboxylate (EPC), 2,2-Bis[4-(2-hydroxy-3-methacryloxypropoxy)phenyl]propane (Bis-GMA), ethoxylated Bis-GMA (EBPDMA), 1,6-bis-[4-(2-hydroxy-3-methacryloyloxypropyl)-phenyl]propane, ethyl-4-N,N-dimethylaminobenzoate (EDMAB), triethylene glycol dimethacrylate (TEGDMA), 1,6-bis-2-methacryloyloxyethoxycarbonylamino]-2,4,4-trimetylhexane (UDMA), dodecanediol dimethacrylate (D3MA), and fluorinated bis-GMA.

2. A method according to claim 1 wherein the polymeric matrix is selected from resins selected from the group consisting of phenolic; amidic; epoxy; polyurethane; unsaturated polyester; cyanoacrylic; silicon; alkylic; acrylic; polycarbonate; thermoplastic polyester; vinylester; vinyl polyfluoride; dendritic resins; and polyolefin resins.

3. A method according to claim 1 wherein the polymerizing agent of part (b) is the diglycidylether of bisphenol A having the following formula I:

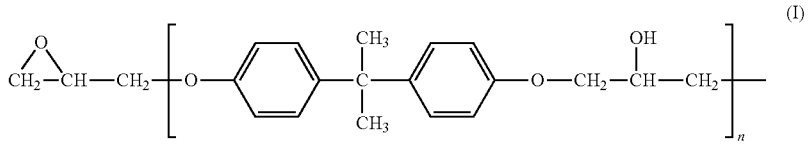

wherein n is less than 2.5.

4. A method according to claim 1 wherein the polymerising agent is in admixture with a reactive diluent selected from the group consisting of 1,4-butanediol diglycidyl ether, neopentyl glycol diglycidyl ether, nonyl phenol glycidyl ether, 2-ethylhexyl glycidyl ether and cyclohexane dimethanol diglycidyl ether.

5. A method according to claim 1 wherein the microcapsules or nanocapsules are made of copolymers of maleic anhydride and polyurea-formaldehyde; polyurethanes; isocyanates with diamines and triamines; or poiyamides.

6. A method according to claim 1 wherein the microcapsules or nanocapsules further contain pharmacologically active compounds.

7. A method according to claim 6 wherein the pharmacologically active compounds are selected from anti-inflammatory, antibiotic or chemotherapeutic agents.

8. A method according to claim 1, further comprising an inorganic compound dispersed within the polymeric matrix and capable to bind an active principle or an inorganic ion.

9. A method according to claim 8 wherein the inorganic compound is a lamellar solid able to intercalate and having a positive or negative charge of the lamellae, said charge being counterbalanced by inorganic anions or inorganic cations.

10. A method according to claim 1 wherein the composite material is used in the preparation of prostheses, dental cements or reconstruction of tissues.

11. A method according.to claim 9 wherein the positive or negative charge of the lamellae is counterbalanced by a fluoride ion or by a calcium ion, respectively.

* * * * *

UNITED STATES PATENT AND TRADEMARK OFFICE
CERTIFICATE OF CORRECTION

PATENT NO.       : 8,795,732 B2
APPLICATION NO.  : 13/140742
DATED            : August 5, 2014
INVENTOR(S)      : Vittoria Vittoria It is certified that error appears in the above-identified patent and that said Letters Patent is hereby corrected as shown below:

On the title page, the Assignee reads:

(73) Assignee: Mario Minale, Naples (IT)

should read:

(73) Assignee: Mario Minale, Naples (IT)
                Vittoria Vittoria, Naples (IT)
                Gianfranco Peluso, Naples (IT)

Signed and Sealed this
Twelfth Day of July, 2016

Michelle K. Lee
*Director of the United States Patent and Trademark Office*